United States Patent [19]

Ritter et al.

[11] Patent Number: 4,670,127
[45] Date of Patent: Jun. 2, 1987

[54] ION-SENSITIVE MEMBRANE ELECTRODE

[75] Inventors: Christoph Ritter; Massoud Ghahramani, both of Graz; Hermann Marsoner, Steinberg, all of Austria

[73] Assignee: AVL AG, Schaffhausen, Switzerland

[21] Appl. No.: 798,959

[22] Filed: Nov. 18, 1985

[30] Foreign Application Priority Data

Jan. 31, 1985 [AT] Austria ................................ 276/85

[51] Int. Cl.$^4$ .............................................. G01N 27/30
[52] U.S. Cl. ..................................... 204/418; 204/1 T
[58] Field of Search ................................ 204/1 B, 418

[56] References Cited

U.S. PATENT DOCUMENTS 4,168,219 9/1979 Hiiro et al. .......................... 204/418
4,349,426 9/1982 Sugahara et al. ................... 204/418

FOREIGN PATENT DOCUMENTS 3000886 7/1980 Fed. Rep. of Germany ...... 204/418
1097928 6/1984 U.S.S.R. ............................. 204/418

Primary Examiner—G. L. Kaplan
Attorney, Agent, or Firm—Watson, Cole, Grindle & Watson

[57] ABSTRACT

In order to produce a sensitive membrane electrode with high selectivity with respect to other anions and lipophilic ions or interfering substances, the membrane is based on an unplasticized polymer matrix whose content of electroactive component is between 50 and 90 percent by weight.

4 Claims, No Drawings

ION-SENSITIVE MEMBRANE ELECTRODE

BACKGROUND OF THE INVENTION

The present invention relates to an ion-sensitive, or rather a chloride-sensitive, membrane electrode comprising an anion-sensitive membrane with one or more electroactive components incorporated into an unplasticized polymer matrix.

DESCRIPTION OF THE PRIOR ART

Ion-sensitive electrodes are sensors with a selective response to ions, utilizing the preferential charge transfer of a particular ion of the sample or sample solution into the membrane phase, and the resulting change of electrochemical potential. Such ion-selective electrodes are widely used for measuring ions even in undiluted body fluids, as this method of measurement has considerable advantages.

Ion-sensitive electrodes of the above type have been discussed in the literature at great length. Karl Carman's book "Das Arbeiten mit ionen-selektiven Elektroden" (Springer-Verlag, Berlin, Heidelberg, New York, 1973), for example, gives a comprehensive survey of the principles and practical applications of a variety of ion-sensitive electrodes, including the use of ion-sensitive electrodes for ion analysis.

Extensive literature also exists on ion measurements in biological fluids, amongst others "Medical and Biological applications of Electrochemical Devices" by Jiri Koryta (John Wiley and Sons, New York, 1980).

Whereas many cation-sensitive electrodes of this type have been used in practical analytical applications for years, the development of anion-sensitive sensors configured as ion-selective electrodes still causes problems. Among the anions which are given routine analysis in biological fluids, for instance, chloride has a dominant position. At a concentration of approximately 0.1 mol/l chloride is the anion most frequently encountered in the extracellular fluid, and thus in blood serum. Together with the bicarbonate ion, which is usually determined from the total amount of $CO_2$, it constitutes the majority of all anions.

The attempt to measure chloride in blood, blood serum, plasma and urine by means of ion-sensitive electrodes dates back to the very beginning of ion-sensitive sensors. Originally, conventional "halide membrane electrodes" were used for this purpose. Electrodes of this type consist of a solid silver body with a coating of silver chloride applied by electrolytic methods. According to the laws of electrochemistry such electrodes are reversible for chloride ions, their potential following Nernst's equation. Together with a suitable reference electrode, such an electrode indeed may be used for measuring chloride in aqueous solutions. Contact with biological fluids will trigger a number of undesirable interferences and side reactions, however, which may not only grossly falsify test results but will also considerably reduce the useful life of the electrode.

Another group of ion-sensitive electrodes, i.e., the so-called liquid membrane electrodes, have proved more successful, in particular for the measurement of chloride. Their main feature is an ion-sensitive membrane essentially consisting of a solution of an electroactive component contained in a suitable membrane matrix, the electroactive components were absorbed in porous substrates, e.g., platelets of an inert filtering material; since the pioneering work by Moody, Oke and Thomas was published (cf. "A Calcium-Sensitive Electrode Based on a Liquid Ion Exchanger in a Polyvinyl Chloride Matrix", Analyst, 95, 910 f (1970), polyvinyl chloride with a generally high plasticizer content has become the membrane material most frequently used.

It is therefore no surprise that a large number of publications and patent literature are devoted to anion-sensitive electrodes for the measurements of chloride, comprising the subsequent basic components:

(1) a solution of a polymer (in particular, PVC) in a suitable solvent, such as tetrahydrofuran or cyclohexanone;

(2) an electroactive substance permitting more or less selective interaction with the chloride ion of the solution;

(3) a plasticizer at a high concentration (i.e., making up a large percentage of the weight of the membrane), rendering the membrane soft and reducing the electrical resistance of such plastic membranes to a useful level of a few hundred meg-ohm.

The electroactive components for the known types of electrodes were mainly selected from the group of quaternary ammonium compounds (chlorides) or quaternary phosphonium chlorides. According to studies, of K. Hartman et al as discussed in "Chloride-Selective Liquid-Membrane Electrodes Based on Lipophilic Methyl Tri-N-Alkyl-Ammonium Compounds and Their Applicability to Blood Serum Measurements", published in Microcimica Acta, pp 235–246 (1978), these quaternary compounds should be applied in such a form that they are allowed to develop strong lipophilic properties, for instance, by attaching alkyl chains of a suitable length, which will make them remain within the membrane and prevent them from entering the sample upon contact with aqueous solutions or solutions that also contain a certain amount of lipophilic substances, such as blood or blood serum, due to a high distribution coefficient in favor of the membrane.

In earlier types of chloride-sensitive liquid membrane electrodes the well-known commercial product "Aliquat 336" was used as an electroactive component, which probably is a methyl-tri-caprylcyl-ammonium chloride; the above studies have shown, however, that methyl-tri-dodecyl-ammonium chloride is preferable. Its advantages are better lipophilic properties due to three dodecyl groups in addition to the methyl group. Although this particular compound is frequently cited in the literature, the present invention does not insist on the exclusive use of methyl-tri-dodecyl-ammonium chloride as electroactive component. Any comparable quaternary ammonium or phosphonium halide compound whose side groups will ensure satisfactory lipophilic properties and a sufficiently long life of the membrane as a consequence, can be used for this purpose.

For manufacture of the known types of membranes a certain percentage of the electroactive component together with polyvinyl chloride and a plasticizer are dissolved in a suitable solvent. By evaporation of the solvent a generally rigid, transparent membrane of a defined geometry is moulded from this mixture. Typical membranes classified as preferable in the literature would contain approximately 29 percent by weight PVC, 65 percent by weight plasticizer, e.g., orthonitrophenyl-octyl-ether or dinitro-butyl-phtalate, etc., and 6 percent by weight electroactive component, e.g., methyl-tri-dodecyl-ammonium chloride.

Data on the known membrane formulations vary throughout the literature and patent specifications. In U.S. Pat. No. 4,349,426, for example, the concentration of methyl-tri-dodecyl-ammonium chloride ranges from 10 to 20 percent by weight, that of the plasticizer n-tetradecyl alcohol from 20 to 40 percent by weight, and that of PVC from 40 to 60 percent by weight. German Laid Open Print No. 30 00 886 specifies a membrane composition of 20 to 24 percent by weight methyl-tri-dodecyl-ammonium chloride, 5 to 15 percent by weight phenyl-alkyl-alcohol as a plasticizer, and 60 to 79 percent by weight polyvinyl chloride dissolved in tetrahydrofuran.

The common feature of all known membrane formulations is that they include at least three basic components:
(1) PVC or another known polymer material suitable for such purposes, e.g., polycarbonate, polymethyl acrylate, silicone rubber, as membrane material.
(2) An electroactive component from the group of tetraalkylammonium chlorides or tetraalkyl-phosphonium chlorides.
(3) A varying, but normally very high, percentage of a suitable plasticizer for the polymer matrix.

As only exception, the publication by K. Hartman et al referred to above, presents two membrane compositions that deviate to a degree from all others. In one composition use of the plasticizer 5-phenyl-1-pentanol amounts to 10 percent by weight only, whereas in the other one no plasticizer is used at all, the only components being 18 percent by weight methyl-tri-dodecyl-ammonium chloride and 82 percent by weight PVC. The latter formulation is presented as functional but not preferable.

If ion-sensitive, in particular chloride-sensitive, electrodes of this type are used problems will arise upon contact with biological fluids, above all with blood serum and urine, due to interferences caused by the presence of other anions, which will lead to false measurement values. Lipophilic anions, e.g., rhodanide (SCN), which may be present in considerable quantities in the urine of strong smokers, are particularly troublesome.

Selectivity tables for a variety of anions are found in the above publication by K. Hartman et al. Besides, it is of importance that such electrodes do not respond to anions of substances which are administered for therapeutical purposes, above all, to bromide, salicylate and ascorbate.

In applications using the known types of membrane electrodes—especially when working with samples of undiluted urine—interferences have often been encountered whose immediate cause is as yet unknown. But even diluted ureine samples have been affected by interferences.

In this context it should be noted that mixtures of two or more electroactive components of different structures which were selected from the main group of quaternary ammonium or phosphonium chlorides, have not brought about any improvement. Certain interferences have been suppressed by providing the ion-sensitive liquid membranes with hydrophilic ion-permeable protective coats made of cellophane, cuprophane or a suitable cellulose ester, or a mixture of such cellulose esters. In spite of these efforts it has not been possible in every case to ensure a satisfactory measurement free of interference.

It should further be noted that a certain selectivity sequence for interfering ions has to be reckoned with when ion exchange salts, e.g., the above quaternary ammonium chlorides, are used. This sequence cannot be changed by the addition of plasticizers, membrane coatings, etc.; the only change possible is in the overall range of the constants. As a consequence, any reduction in interference activities of ions with selectivity constants K greater than 1 will impair selectivity vis-á-vis interfering ions with selectivity constants K smaller than 1.

SUMMARY OF THE INVENTION

It is an object of the present invention to develop an ion-sensitive membrane electrode of the above type in such a way as to improve its selective characteristics regarding the ion to be detected, without having to put up with the disadvantages of the known types of membrane electrodes. Above all, a simple chloride-sensitive membrane electrode should be developed, with high selectivity vis-á-vis other anions and lipophilic ions in blood as well as other interfering substances in body fluids.

According to the invention this aim is achieved by increasing the content of the electroactive component in the membrane to 50 to 90 percent by weight. This formulation makes use of the surprising discovery that the selective characteristics of the above liquid membranes may be dramatically improved by completely eliminating from the polymer matrix all plasticizers normally included in state-of-the-art compositions, and by radically increasing the content of the electroactive component to more than 50 percent by weight instead.

For membrane electrodes made from PVC as a polymer matrix and methyl-tri-dodecyl-ammonium chloride as an electroactive component, in particular, it has proved of advantage if the content of the electroactive component in the membrane is 60 to 80 percent by weight, as proposed in a preferred variant of the invention.

In view of the known types of membranes and of the above publication by K. Hartman al, in which the unplasticized membrane is referred to as a non-advantageous variant, the formulation of an anion-sensitive membrane as specified by the invention signifies that a prejudice of the experts has been overcome, although the theory behind the success of the new formulation can only be guessed at for the time being.

The unexpected properties and advantages of ion-sensitive membrane electrodes according to the invention are indicated in Table 1 below, in which the selectivities and interferences of a number of anions vis-á-vis chloride are given for three different membrane compositions.

The membrane compositions are:
(1) A conventional plasticized electrode membrane (e.g., 27 percent by weight methyl-tri-dodecyl-ammonium chloride, 5 percent by weight 2-nitroparacymene and 5 percent by weight 5-phenyl-1-pentanol as plasticizing agents, and 63 percent by weight PVC).
(2) An unplasticized membrane with 80 percent by weight PVC and 20 percent by weight tri-dodecyl-ammonium chloride, in accordance with the disclosure by K. Hartman et al, referred to above.
(3) A membrane according to the present invention, consisting of 80 percent by weight tri-dodecyl-ammonium chloride and 20 percent by weight PVC.

In all instances the selectivity constant has been determined by the fixed interference method FIM.

TABLE 1

Typical selectivity data for various membrane compositions (as shown as logarithms of selectivity constants)

| Ion | Membrane 1 | Membrane 2 | Membrane 3 |
| --- | --- | --- | --- |
| $ClO_4$ | — | 3.7 | 0.6 |
| I | 1.77 | — | 0.32 |
| $NO_3$ | 1.0 | 1.6 | 0.56 |
| Br | 0.62 | 1.0 | 0.19 |
| $NO_2$ | 0.65 | 0.7 | 0.51 |
| $HCO_3$ | −1.17 | −1.0 | −0.045 |

Selectivity data as seen in Table 1 indicate that there are ions for which the membrane electrode specified by the invention has a selectivity which is higher than that for the chloride. In combination with suitable measuring media an ion-sensitive membrane electrode as specified by the invention can therefore be used for measuring other ions as well, e.g., $ClO_4$, SCN, iodide, $NO_3$, bromide. The advantages to be gained in each instance will depend on the special composition of the solution to be measured. In physiological solutions a membrane electrode according to the invention is best used for measuring chloride, due to the concentration ratios of the individual ions.

In this context it should be noted that ion-sensitive membrane electrodes may also be provided with suitably charged electroactive components which are of advantage for diverse purposes. The electrical resistance of the membrane obtained in this way is relatively low (0.1–1 meg-ohm), which will make the membrane electrode easy to use for measuring purposes, and is probably due to the comparatively high density of electrical charge in the membrane.

The advantages of an electrode designed according to the invention can also be seen from a comparison of chloride measurements in urine samples.

Table 2 presents the results of a chloride test performed on five urine samples by means of (a) a conventional colorimetric method, and (b) a conventional plasticized electrode membrane (membrane 1 in Table 1). For the colorimetric method the urine samples are entered undiluted; the necessary dilution is performed automatically by the test equipment. "Membrane 1" did not permit a useful analysis of undiluted urine due to strong drifting caused by interfering ions—the samples had to be diluted therefore (2 parts diluting agent / 1 part urine).

TABLE 2

| Sample | Colorimetry | Membrane 1 |
| --- | --- | --- |
| 1 | 66 m mol/l | 347 m mol/l |
| 2 | 85 | 95 |
| 3 | 99 | 154 |
| 4 | 136 | 309 |

TABLE 2-continued

| Sample | Colorimetry | Membrane 1 |
| --- | --- | --- |
| 5 | 176 | 228 |

The marked differences in the values obtained by the two methods would be even more pronounced if undiluted samples were measured with membrane 1.

Table 3 presents test results obtained by the colorimetric method and with the use of an unplasticized electrode membrane (membrane 2 in Table 1).

TABLE 3

| Sample | Colorimetry | Membrane 2 |
| --- | --- | --- |
| 1 | 16 m mol/l | 1117 (617) m mol/l |
| 2 | 43 | 86 |
| 3 | 79 | 119 |
| 4 | 91 | 130 |
| 5 | 119 | 400 |

For the test performed with membrane 2 the sample again was diluted at a ratio of 2:1.

Table 4 presents results obtained with the use of an electrode membrane as proposed by the invention (membrane 3 in Table 1).

TABLE 4

| Sample | Colorimetry | Membrane 3 |
| --- | --- | --- |
| 1 | 39 m mol/l | 43 m mol/l |
| 2 | 70 | 75 |
| 3 | 91 | 93 |
| 4 | 170 | 169 |
| 5 | 233 | 241 |

This comparison shows clearly that with the use of a membrane electrode as specified by the invention the chloride test can also be performed on undiluted urine, without the significant deviations in measured values experienced with conventional membrane electrodes.

We claim:

1. An ion-sensitive membrane electrode which includes an anion-sensitive membrane, said anion-sensitive membrane containing no plasticizer component and comprising an unplasticized polymer matrix which consists of an unplasticized polyvinyl chloride matrix and between 50 and 90% by weight of at least one electroactive component incorporated in said polyvinyl chloride matrix, said electroactive component being selected from the group consisting of a quaternary ammonium compound and a phosphonium halide compound.

2. An ion-sensitive membrane electrode according to claim 1, wherein said electroactive component incorporated in said unplasticized polyvinyl chloride matrix is methyl-tri-dodecyl-ammonium chloride.

3. An ion-sensitive membrane electrode according to claim 2, wherein said anion-sensitive membrane includes 60 to 80% by weight of said methyl-tri-dodecyl-ammonium chloride.

4. An ion-sensitive membrane electrode according to claim 1, wherein said anion-sensitive membrane is sensitive to chloride ions.

* * * * *